United States Patent [19]

Chauvin et al.

[11] 4,424,282

[45] Jan. 3, 1984

[54] PROCESS FOR THE CATALYTIC SYNTHESIS OF HYDROCARBONS, PARTICULARLY OF METHANE, FROM HYDROGEN AND CARBON MONOXIDE

[75] Inventors: Yves Chauvin, Le Pecq; Dominique Commereuc, Meudon; Andre Sugier; Jean-Francois Le Page, both of Rueil Malmaison, all of France

[73] Assignee: Institut Francais du Petrole, Rueil-Malmaison, France

[21] Appl. No.: 348,890

[22] Filed: Feb. 16, 1982

[30] Foreign Application Priority Data

Feb. 11, 1981 [FR] France ................................. 81 02718

[51] Int. Cl.³ ............................................... C07C 1/04
[52] U.S. Cl. .................................... 518/700; 518/711; 518/714; 518/712
[58] Field of Search ............... 518/700, 715, 713, 714, 518/711, 712

[56] References Cited

U.S. PATENT DOCUMENTS

| 2,535,060 | 12/1950 | Gresham | 518/700 |
| 2,549,470 | 4/1951 | Howk et al. | 518/700 |
| 2,617,816 | 11/1952 | Crowell et al. | 518/700 |
| 2,632,014 | 3/1953 | Gresham | 518/700 |
| 3,930,812 | 1/1976 | Harris et al. | 518/712 |
| 4,171,320 | 10/1979 | Vannice et al. | 518/715 |
| 4,206,134 | 6/1980 | Kugh et al. | 518/715 |

FOREIGN PATENT DOCUMENTS 1516319  7/1978  United Kingdom ................ 518/715

Primary Examiner—Howard T. Mars
Attorney, Agent, or Firm—Millen & White

[57] ABSTRACT

Methane is produced by passing hydrogen, carbon monoxide and an aqueous liquid phase downwardly through a fixed bed of a catalyst containing ruthenium on a carrier such as alumina, separating and externally coolng in a heat exchanger the resultant aqueous phase before recycling, thereby limiting the reaction temperature within a range from 200° to 320° C.

10 Claims, No Drawings

PROCESS FOR THE CATALYTIC SYNTHESIS OF HYDROCARBONS, PARTICULARLY OF METHANE, FROM HYDROGEN AND CARBON MONOXIDE

The present invention has for an object a catalytic process for synthesizing hydrocarbons, particularly methane, from hydrogen and carbon monoxide.

It is well known that hydrocarbons can be obtained by contacting carbon monoxide with hydrogen, in the presence of a ruthenium containing catalyst. Particularly methane can be obtained according to the main reaction:

$$CO + 3H_2 \rightleftharpoons CH_4 + H_2O$$

Secondary reactions may also occur, particularly the conversion of CO to $CO_2$ by the action of steam and the conversion of $CO_2$ to $CH_4$ by the action of hydrogen.

The main difficulty to overcome when carrying out these reactions results from their highly exothermic character which requires a very efficient removal of the produced heat, in order to avoid a rapid decrease of the catalyst activity.

The known gas phase processes are not favorable to an efficient heat removal and require the dilution of the reactants, generally with the output gases from the reactor, which makes the process considerably more complicated to perform.

It has also been proposed to operate by maintaining a hydrocarbon synthesis solid catalyst in a liquid hydrocarbon phase used to remove the heat produced by the reaction.

The liquid phase to be used must have thermal stability and chemical inertness both with respect to the reactants and to the water produced in the reaction and with respect to the catalyst involved. Usually, there are used saturated hydrocarbons or paraffinic or aromatic oil cuts. These diluents must in most cases be purified, particularly by removal of their sulfur-containing impurities which are generally detrimental to the activity and the life of the catalyst (U.S. Pat. No. 3,989,734).

This is a first disadvantage of using diluents. A second disadvantage, much more serious, results from their poor stability over a long time period, resulting from secondary cracking, hydrogenolysis or polymerization reactions. It is thus necessary to make use of a system for purifying the diluent, for example by providing for the removal of a portion of the used diluent and its replacement with fresh diluent, thereby increasing the cost of synthesis operation accordingly. The degradation of the diluent liquid phase is usually accompanied with the formation of deposits of heavy compounds, or even carbon, at the catalyst surface, thus reducing its activity.

The use of $H_2O$ in the liquid phase as a heat transfer fluid (U.S. Pat. No. 3,930,812) makes it possible, to a certain extent, to avoid the above-mentioned disadvantages. It is however necessary, for this purpose, that dry zones be not liable to appear and, accordingly, the trickling technique involves serious risks.

The present invention has for an object a process for converting carbon monoxide and hydrogen to hydrocarbons and, more particularly, to methane, in the presence of a ruthenium supported catalyst, in a fixed bed, in contact with a liquid phase consisting essentially of water in loop circulation through the catalyst bed and then through a heat exchange system external to the catalyst bed.

In the process, the water may flow through the catalyst bed either upwardly or downwardly.

A portion of this water is unavoidably driven as steam along with the output gases, wherefrom it can be easily condensed and optionally recycled. Nevertheless the water flow rate through the reactor and the external heat exchanger is so adjusted that at least the major part of the heat evolved from the reaction is removed as sensible heat by the liquid phase.

It is important that the catalyst be immersed as completely as possible in water in order to provide for a good liquid-solid contact which avoids the occurrence of dry zones which would lead to hot points in the catalyst and to thermal instability of the catalyst bed. This instability would unavoidably result in a reduction of the catalyst life time.

It has been found that the best selectivity to methane and the longest life time of the catalyst are obtained with a downward flow through the reactor both of the gaseous reactants and the water.

By means of this technique, it is possible to obtain in a single run high conversions of the hydrogen-carbon monoxide synthesis mixture.

The catalyst used according to the invention contains ruthenium or at least one ruthenium compound deposited on an inorganic carrier such, for example, as silica, alumina, a silica-alumina, an aluminate, thoria, zirconia, magnesia, titanium oxide and natural or synthetic zeolites. The preferred carrier is a $\gamma$ alumina. The carrier may be shaped arbitrarily as grains, balls or extrudates, for example of 0.5 to 5 mm. The ruthenium deposit may be effected by conventional methods well known in the art, for example by impregnation with an aqueous solution of ruthenium trichloride. Further calcination and reduction treatments may be effected in order to improve the activity. The ruthenium content may, for example, be from 0.1 to 5% by weight.

Another preferred carrier is charcoal.

The catalyst may contain, in addition to ruthenium, various other metals having a co-catalytic effect, for example another noble metal, nickel, cobalt, tugnsten, molybdenum or rhenium The composition of the systhesis gas mixture, expressed by the hydrogen/carbon monoxide molar ratio may be from 0.2/1 to 6/1. The operation is preferably conducted with a ratio of 2.5/1 to 5/1 when it is desired to selectively form methane, and more particularly a ratio close to 3/1, which corresponds to the theoretical stoichiometry of the reaction. However, a higher ratio is not detrimental for the methane selective synthesis.

When the composition of the synthesis gas mixture is such that the hydrogen/carbon monoxide ratio is clearly lower than 2.5/1, for example 1/1, methane is still produced as the main product. However, there is also formed gaseous hydrocarbons: ethane, propane, butanes and saturated liquid hydrocarbons up to $C_{20}$, which constitute a very good steam-cracking charge.

It is however possible to increase the methane production even with $H_2/CO$ ratios lower than 2.5/1, for example with ratios ranging from 1/1 to 2.5/1, by simultaneously effecting a partial conversion of CO with water to $H_2$ and $CO_2$, with the use of an additional catalyst for this conversion, for example a catalyst of chromium and zinc oxides or copper oxide.

The reaction temperature may be selected from 100° to 350° C., preferably from 200° to 320° C., more particularly from 220° to 280° C.

The total pressure in the reactor may be selected from 1 MPa to 15 MPa, preferably at such a value that, by taking into account the water vapor pressure at the selected temperature, the partial pressure of the hydrogen-carbon monoxide mixture be from 0.1 MPa to 10 MPa, preferably from 0.1 to 2 MPa when it is desired to obtain preferentially methane.

The hourly space velocity, expressed in volume of gas mixture (CO+H$_2$), under normal conditions, fed per volume of catalyst and per hour (VVH) may vary from 1 to 20 000. Preferably, the operation is conducted with a VVH from 100 to 8 000.

The flow rate of water feeding the reactor, expressed in volume of liquid water per volume of catalyst and per hour, is at least 1 volume per volume and per hour. Preferably, the flow rates are from 1 to 100 volumes per volume and per hour.

The following examples illustrate the invention without however limiting the scope thereof.

The reactor used for the test described below is a part of a micropilot unit providing for a continuous operation. The reactor consists of a stainless steel tube of 100 cc capacity. The synthesis gas mixture and water may be injected at will either at the top or at the bottom of the reactor.

EXAMPLE 1

A ruthenium containing catalyst has been prepared by impregnation of γ-alumina in the form of extrudates of 1 mm (specific surface: 250 m$^2$/g) by means of an aqueous solution of ruthenium trichloride. The catalyst obtained after calcination and reduction with hydrogen at 450° C. has a ruthenium content of 4.5% by weight. 15 cc of this catalyst, diluted with an equal volume of carborundum balls, are charged in the above-described reactor.

There is then introduced a synthesis gas having a H$_2$/CO ratio by volume of 3/1, at a rate of 50 l (NTP)/h from the top of the reactor. Water is also introduced from the top at a rate of 40 g/h. The other operating conditions as well as the results are reported in Table I.

The results are expressed by:

The conversion rate C, in % by mole, defined as:

$$C (\%) = \frac{CH_4 + \sum_{i=2}^{n} iC_iH_{2i+1} + CO_2}{CO \text{ (input)}} \times 100$$

The selectivity $S_{HC}$ to hydrocarbons, in % by mole, defined as:

$$S_{HC}(\%) = \frac{CH_4 + \sum_{i=2}^{n} iC_iH_{2i+1}}{CH_4 + \sum_{i=2}^{n} iC_iH_{2i+1} + CO_2} \times 100$$

the methane fraction $S_{CH4}$, in % by mole, defined as:

$$S_{CH4} (\%) = \frac{CH_4}{CH_4 + \sum_{i=2}^{n} iC_iH_{2i+1}} \times 100$$

It is observed that at a temperature higher than about 210° C., the conversion of carbon monoxide is complete. In these conditions, the selectivity to methane is very high.

EXAMPLE 2

15 cc of the catalyst prepared in example 1 and diluted in the same manner are charged in the same reactor as precedingly. The synthesis gas is then introduced at a H$_2$/CO ratio by volume of 3/1, except for the period 25–35 h where the ratio is 1/1, together with water, at the bottom of the reactor. The flow rates are substantially equal to those of example 1. The operating conditions and the results are reported in Table 2.

It is observed again that the conversion rate of carbon monoxide is high at a temperature exceeding about 210° C. However, the selectivity to methane is lower than when the injection is made at the top of the reactor as in example 1.

It is also observed that, in the period 25–35 h, where the synthesis gas has a H$_2$/CO ratio by volume of 1/1, the methane selectivity is lower. During this period, it has been observed that higher hydrocarbons are formed, in the following proportions:

| methane | 47.4% by weight |
|---|---|
| ethane + propane + butanes | 45.2% by weight |
| liquid hydrocarbons | 7.4% by weight |

EXAMPLE 3

This example is given by way of comparison and forms no part of the invention. The operating conditions and the catalyst were the same as in example 1 except that water was replaced with a cut of saturated hydrocarbons (boiling point from 280° to 340° C. under 760 mm Hg). After 50 h of run at 220° C. under a pressure of 2.5 MPa, i.e. at a partial pressure of CO and H$_2$ of 0.2 MPa, the carbon monoxide conversion, initially of 100%, was reduced to 40%.

TABLE 1

| RUN-NING TIME (h) | T (°C.) | TOTAL P(MPa) | P(CO + H$_2$) (MPa) | C % | $S_{HC}$ % | $S_{CH4}$ % |
|---|---|---|---|---|---|---|
| 0–2 | 220 | 2.5 | 0.2 | 100 | 98.4 | 97.6 |
| 2–20 | 220 | 2.5 | 0.2 | 100 | 95.7 | 98.9 |
| 20–25 | 220 | 2.5 | 0.2 | 100 | 96 | 99 |
| 25–50 | 220 | 2.5 | 0.2 | 100 | 95.9 | 98.8 |
| 50–70 | 200 | 4.0 | 2.4 | 37.9 | 100 | 79.7 |

TABLE 2

| RUN-NING TIME (h) | T (°C.) | TOTAL P (MPa) | P(CO + H$_2$) (MPa) | C % | $S_{HC}$ % | $S_{CH4}$ % |
|---|---|---|---|---|---|---|
| 0–5 | 155 | 1.1 | 0.1 | 1.3 | 100 | 76.6 |
| 5–10 | 215 | 2.5 | 0.5 | 33.2 | 100 | 70.7 |
| 10–15 | 260 | 4.5 | 0.1 | 100 | 99 | 84.4 |
| 15–20 | 210 | 2.5 | 0.7 | 82.4 | 100 | 70.9 |
| 20–25 | 220 | 2.5 | 0.2 | 99.3 | 100 | 74.9 |
| 25–35* | 210 | 2.9 | 1.1 | 21.1 | 80.7 | 48.4 |

*H$_2$/CO = 3/1 by volume from 0 to 25 h, H$_2$/CO = 1/1 by volume from 25 to 35 h.

What is claimed is:

1. A process for manufacturing methane by reacting hydrogen with carbon monoxide in the presence of a ruthenium-containing catalyst, comprising circulating hydrogen, carbon monoxide and an aqueous liquid phase consisting essentially of water through a fixed bed of a catalyst containing ruthenium on a carrier at a temperature from 200° to 320° C., at a total pressure from 1 to 15 MPa, and at a partial pressure of the ($CO+H_2$) mixture from 0.1 to 2 MPa, said aqueous liquid phase being circulated in a non-trickling manner and at a flow rate to maintain the catalyst substantially immersed therein; separating the resultant gaseous phase from the resultant aqueous liquid phase; passing the aqueous liquid phase through a heat exchanger outside the reaction zone for cooling said aqueous phase; and recycling the cooled aqueous phase, at least the major part of the heat produced by the reaction being removed in said exchanger by means of the sensible heat of the circulating aqueous liquid phase.

2. A process according to claim 1, wherein the hydrogen, the carbon monoxide and the aqueous phase flow downwardly in the reactor.

3. A process according to claim 1, wherein the hourly flow rate of gas ($H_2+CO$) is from 100 to 8 000 volumes (NTP) per catalyst volume, the water hourly flow rate is from 1 to 100 volumes per volume of catalyst.

4. A process according to claim 3, wherein the molar ratio $H_2/CO$ is from 2.5/1 to 5/1.

5. A process acccording to claim 1, wherein the catalyst is in the form of particles having a size from 0.5 to 5 mm.

6. A process according to claim 1, wherein the catalyst comprises 0.1 to 5% by weight of ruthenium on alumina.

7. A process according to claim 6, wherein the alumina is $\gamma$-alumina.

8. A process according to claim 6, wherein the catalyst is obtained by incorporating an aqueous solution of ruthenium trichloride to the alumina.

9. A process according to claim 1, wherein said temperature is from 220° to 280° C.

10. A process according to claim 7 wherein the catalyst is in the form of extrudates and has a ruthenium content of 4.5%, the catalyst is mixed with an equal volume of carborundum balls, said temperature is 220° C., said total pressure is 2.5 MPa and said partial pressure is 0.2 MPa.

* * * * *

UNITED STATES PATENT AND TRADEMARK OFFICE
CERTIFICATE OF CORRECTION

PATENT NO. : 4,424,282

DATED : January 3, 1984

INVENTOR(S) : Yves Chauvin et al

It is certified that error appears in the above-identified patent and that said Letters Patent is hereby corrected as shown below:

Column 5, line 22: reads "is from 1 to 100 volumes per volume of catalyst."

should read -- is from 1 to 100 volumes per volume of catalyst and the molar ratio $H_2/CO$ from 1/1 to 5/1. --

Signed and Sealed this

Fifth Day of June 1984

[SEAL]

Attest:

GERALD J. MOSSINGHOFF

Attesting Officer

Commissioner of Patents and Trademarks